(12) United States Patent
Shepherd

(10) Patent No.: US 8,657,876 B2
(45) Date of Patent: Feb. 25, 2014

(54) METHODS AND APPARATUS FOR INSERTING AN INTRAOCULAR LENS INTO AN EYE

(75) Inventor: David J. Shepherd, San Juan Capistrano, CA (US)

(73) Assignee: Abbott Medical Optics, Inc., Santa Ana, CA (US)

( * ) Notice: Subject to any disclaimer, the term of this patent is extended or adjusted under 35 U.S.C. 154(b) by 125 days.

(21) Appl. No.: 13/022,329

(22) Filed: Feb. 7, 2011

(65) Prior Publication Data

US 2011/0152873 A1 Jun. 23, 2011

Related U.S. Application Data

(63) Continuation of application No. 11/102,194, filed on Apr. 8, 2005, now Pat. No. 7,892,282.

(51) Int. Cl.
*A61F 2/16* (2006.01)

(52) U.S. Cl.
USPC .......................................... 623/6.12; 606/107

(58) Field of Classification Search
USPC ............................ 623/6.12; 606/107; 269/262
See application file for complete search history.

(56) References Cited

U.S. PATENT DOCUMENTS

| 2,605,766 | A | * | 8/1952 | Uytenbogaart | ............... | 604/136 |
|---|---|---|---|---|---|---|
| 4,681,102 | A | | 7/1987 | Bartell | | |
| 4,699,140 | A | | 10/1987 | Holmes et al. | | |
| 4,765,329 | A | | 8/1988 | Cumming et al. | | |
| 4,836,201 | A | * | 6/1989 | Patton et al. | .................. | 606/107 |
| 4,852,566 | A | | 8/1989 | Callahan et al. | | |
| 4,862,855 | A | | 9/1989 | Manaka et al. | | |
| 4,919,130 | A | | 4/1990 | Stoy et al. | | |
| 4,934,363 | A | | 6/1990 | Smith et al. | | |
| 4,976,716 | A | | 12/1990 | Cumming | | |
| 5,066,297 | A | | 11/1991 | Cumming | | |

(Continued)

FOREIGN PATENT DOCUMENTS

| EP | 363213 A2 | 4/1990 |
|---|---|---|
| EP | 937443 A2 | 8/1999 |

(Continued)

OTHER PUBLICATIONS

Data Sheet for the UnfolderTM Emerald implantation System (Multilingual) 2005.

(Continued)

*Primary Examiner* — S. Thomas Hughes
*Assistant Examiner* — Julie A Szpira
(74) *Attorney, Agent, or Firm* — Abbott Medical Optics Inc.

(57) ABSTRACT

Apparatus and methodology for inserting an intraocular lens (IOL) into an eye. The apparatus includes a cartridge for holding an IOL and a handpiece with a body member for receiving the cartridge, an injector rod that is receivable by the body member, and a drive mechanism that longitudinally oscillates the injector rod in the body member when a rotational force is applied about a longitudinal axis in a single direction. In other words, a constant rotation in a single direction of the drive mechanism causes the injector rod to move distally and proximally in discrete increments, with the distal increments being larger than the proximal increments. Accordingly, the injector rod urges an IOL out of the handpiece in a two-steps-forward, one-step-back manner, thereby minimizing or eliminating the chance of the injector rod engaging with the IOL.

7 Claims, 10 Drawing Sheets

(56) References Cited

U.S. PATENT DOCUMENTS

| | | | |
|---|---|---|---|
| 5,190,552 A | 3/1993 | Kelman | |
| 5,275,604 A | 1/1994 | Rheinish et al. | |
| 5,443,198 A | 8/1995 | Viola et al. | |
| 5,496,328 A | 3/1996 | Nakajima et al. | |
| 5,499,987 A | 3/1996 | Feingold | |
| 5,582,613 A | 12/1996 | Brady et al. | |
| 5,616,148 A | 4/1997 | Eagles et al. | |
| 5,620,450 A | 4/1997 | Eagles et al. | |
| 5,643,276 A * | 7/1997 | Zaleski | 606/107 |
| 5,653,715 A | 8/1997 | Reich et al. | |
| 5,735,858 A | 4/1998 | Makker et al. | |
| 5,766,181 A | 6/1998 | Chambers et al. | |
| 5,772,667 A | 6/1998 | Blake | |
| 5,776,138 A | 7/1998 | Vidal et al. | |
| 5,800,442 A | 9/1998 | Wolf et al. | |
| 5,807,400 A | 9/1998 | Chambers et al. | |
| 5,843,091 A * | 12/1998 | Holsinger et al. | 606/108 |
| 5,860,984 A | 1/1999 | Chambers et al. | |
| 5,868,752 A | 2/1999 | Makker et al. | |
| 5,873,879 A | 2/1999 | Figueroa et al. | |
| 5,876,406 A | 3/1999 | Wolf et al. | |
| 5,876,407 A | 3/1999 | Makker et al. | |
| 5,921,989 A | 7/1999 | Deacon et al. | |
| 5,928,245 A | 7/1999 | Wolf et al. | |
| 5,947,976 A | 9/1999 | Van Noy et al. | |
| 6,001,107 A | 12/1999 | Feingold | |
| 6,010,510 A | 1/2000 | Brown et al. | |
| 6,048,348 A | 4/2000 | Chambers et al. | |
| 6,059,791 A | 5/2000 | Chambers | |
| 6,074,397 A | 6/2000 | Chambers et al. | |
| 6,174,315 B1 | 1/2001 | Chambers et al. | |
| 6,179,843 B1 | 1/2001 | Weiler | |
| 6,203,549 B1 | 3/2001 | Waldock | |
| 6,251,114 B1 | 6/2001 | Farmer et al. | |
| 6,254,607 B1 | 7/2001 | Makker et al. | |
| 6,267,768 B1 | 7/2001 | Deacon et al. | |
| 6,270,514 B1 | 8/2001 | McDonald | |
| 6,273,894 B1 | 8/2001 | Dykes | |
| 6,280,449 B1 | 8/2001 | Blake | |
| 6,283,975 B1 | 9/2001 | Glick et al. | |
| 6,283,976 B1 | 9/2001 | Portney | |
| 6,312,433 B1 | 11/2001 | Butts et al. | |
| 6,334,862 B1 | 1/2002 | Vidal et al. | |
| 6,336,932 B1 | 1/2002 | Figueroa et al. | |
| 6,355,046 B2 | 3/2002 | Kikuchi et al. | |
| 6,387,101 B1 | 5/2002 | Butts et al. | |
| 6,398,789 B1 | 6/2002 | Capetan | |
| 6,428,545 B2 | 8/2002 | Portney | |
| 6,558,395 B2 | 5/2003 | Hjertman et al. | |
| 6,572,643 B1 | 6/2003 | Gharibadeh | |
| 6,629,979 B1 | 10/2003 | Feingold et al. | |
| 6,666,871 B2 | 12/2003 | Kikuchi et al. | |
| 6,685,740 B2 | 2/2004 | Figueroa et al. | |
| 6,712,848 B1 | 3/2004 | Wolf et al. | |
| 6,849,084 B2 | 2/2005 | Rabkin et al. | |
| 6,866,669 B2 | 3/2005 | Buzzard et al. | |
| 6,923,815 B2 | 8/2005 | Brady et al. | |
| 2001/0001822 A1 | 5/2001 | Chambers et al. | |
| 2001/0007075 A1 | 7/2001 | Hjertman et al. | |
| 2001/0015593 A1 | 8/2001 | Polla et al. | |
| 2002/0151904 A1 | 10/2002 | Feingold et al. | |
| 2002/0165610 A1 | 11/2002 | Waldock | |
| 2002/0173756 A1 | 11/2002 | Waldock | |
| 2002/0193805 A1 | 12/2002 | Ott et al. | |
| 2003/0040755 A1 | 2/2003 | Meyer | |
| 2003/0074045 A1 | 4/2003 | Buzzard et al. | |
| 2003/0176870 A1 | 9/2003 | Ott | |
| 2003/0187455 A1 | 10/2003 | Kobayashi et al. | |
| 2003/0191516 A1 | 10/2003 | Weldon et al. | |
| 2004/0059343 A1 | 3/2004 | Shearer et al. | |
| 2004/0127912 A1 | 7/2004 | Rabkin et al. | |
| 2004/0147938 A1 | 7/2004 | Dusek et al. | |
| 2005/0049607 A1 | 3/2005 | Hart et al. | |
| 2006/0184181 A1 | 8/2006 | Cole et al. | |
| 2006/0229633 A1 | 10/2006 | Shepherd | |
| 2006/0229634 A1 | 10/2006 | Shepherd | |

FOREIGN PATENT DOCUMENTS

| | | |
|---|---|---|
| EP | 1380271 A1 | 1/2004 |
| WO | WO9615743 A1 | 5/1996 |
| WO | WO9620662 A1 | 7/1996 |
| WO | WO9637152 A1 | 11/1996 |
| WO | WO9933411 A1 | 7/1999 |
| WO | WO9937247 A1 | 7/1999 |
| WO | WO03049645 A2 | 6/2003 |
| WO | WO03068302 A2 | 8/2003 |
| WO | WO2004091447 A2 | 10/2004 |
| WO | WO2004105648 A1 | 12/2004 |

OTHER PUBLICATIONS

International Search Report for Application No. PCT/US2005/12787, mailed on Aug. 11, 2006, 3 pages.

\* cited by examiner

METHODS AND APPARATUS FOR INSERTING AN INTRAOCULAR LENS INTO AN EYE

This application is a continuation application and claim priority to U.S. application Ser. No. 11/102,194, filed on Apr. 8, 2005, which is hereby incorporated by reference in its entirety for all purposes as if fully set forth herein.

BACKGROUND OF THE INVENTION

The present invention relates to apparatus and methodology for inserting an intraocular lenses (IOL) into an eye.

The human eye is susceptible to numerous disorders and diseases, a number of which attack the crystalline lens. For example, cataracts mar vision through cloudy or opaque discoloration of the lens of the eye. Cataracts often result in partial or complete blindness. A damaged crystalline lens can be removed and replaced with an intraocular lens, or IOL.

An IOL is implanted in the eye, for example, as a replacement for the natural crystalline lens after cataract surgery or to alter the optical properties of (i.e., provide vision correction to) an eye in which the natural lens remains. IOLs often include a disk-like optic typically including an optically clear lens. Many IOLs also include at least one flexible fixation member or haptic which extends radially outward from the optic and becomes affixed in the eye to secure the lens in position. Implantation of IOLs into the eye involves making an incision in the eye. To reduce trauma and to speed healing, it is advantageous to minimize the size the incision.

The optics may be constructed of rigid biocompatible materials such as polymethyl methacrylate (PMMA) or deformable materials such as silicone polymeric materials, acrylic polymeric materials, hydrogel polymeric materials, and the like. Deformable materials allow the IOL to be rolled or folded for insertion through a small incision into the eye. A substantial number of instruments have been proposed to aid in inserting such a foldable lens in the eye. In a popular apparatus, the optic is folded into a hard-shelled taco and pushed through an insertion tube, progressively compressing the IOL to fit through the incision.

The two primary IOL materials are silicone and acrylic. Silicone IOLs are more pliable and can be compressed to pass through smaller insertion tubes without unduly stressing the insertion tube or IOL, or requiring excessive push force which can violently expel the IOL from the cartridge. Acrylic lenses are indicated for some patients and are inserted in much the same way as silicone IOLs, although generally using larger insertion tubes with larger bore diameters to mitigate the problems caused by the lower flexibility of the acrylic. Because the insertion tubes are larger, the incision sizes are also necessarily larger.

In view of the foregoing, there is a continued need in the art for beneficial advancements in IOL insertion apparatus and methodology.

SUMMARY OF THE INVENTION

According to one aspect of the invention, an apparatus for inserting an intraocular lens (IOL) into an eye includes a load chamber for receiving the IOL and a handpiece. The load chamber is preferably disposed to receive the IOL and for delivery of the IOL into the eye of a subject. The load chamber is preferably contained within a separate housing or cartridge that is attached by a practitioner as part of a surgical procedure. Alternatively, the load chamber may be a part of the handpiece or be contained within a separate housing or cartridge that is mounted to the handpiece prior to shipment to the practitioner. In the latter case, the housing or cartridge is preferably preloaded with the IOL prior to shipment. The load chamber includes a hollow passage with an ejection port through which an IOL is passable.

The handpiece includes a body member that may be configured for receiving the load chamber, an injector rod that is receivable by the body member, and a drive mechanism. The injector rod is longitudinally movable within the load chamber and has a distal portion that is adapted to contact the IOL when positioned within the hollow passage. The drive mechanism is configured to longitudinally or linearly oscillate the injector rod in the body member when a rotational force is applied about a longitudinal axis in a single direction. Accordingly, the IOL is incrementally urged, for example, in discrete increments, by the injector rod into an eye.

One advantage of the incremental urging is the reduction or elimination of the possibility of the injector rod engaging with the IOL or engaging the IOL by an amount that is greater than a predetermined limit. For example, in the latter case, when the injector rod tip is moved a distal increment and is pushed beyond the edge of the IOL, e.g., by advancing the rod tip about 0.10 inch, then the injector rod is subsequently moved away from the IOL by a proximal increment, e.g., by retracting the rod tip by about 0.05 inch. Accordingly, the proximal movement of the injector rod tip allows the IOL to recover to a certain extent under its own resiliency.

According to another aspect of the invention, the drive mechanism may include one or more bosses disposed on the body member and a drive member operatively coupled with the injector rod. The drive member may include a corresponding number of annular races for engaging with the bosses when the injector rod is at least partially received in a through channel of the body member.

Other features and advantages of the present invention will become apparent to those skilled in the art from a consideration of the following detailed description taken in conjunction with the accompanying drawings.

DETAILED DESCRIPTION OF THE INVENTION

Figure 1:
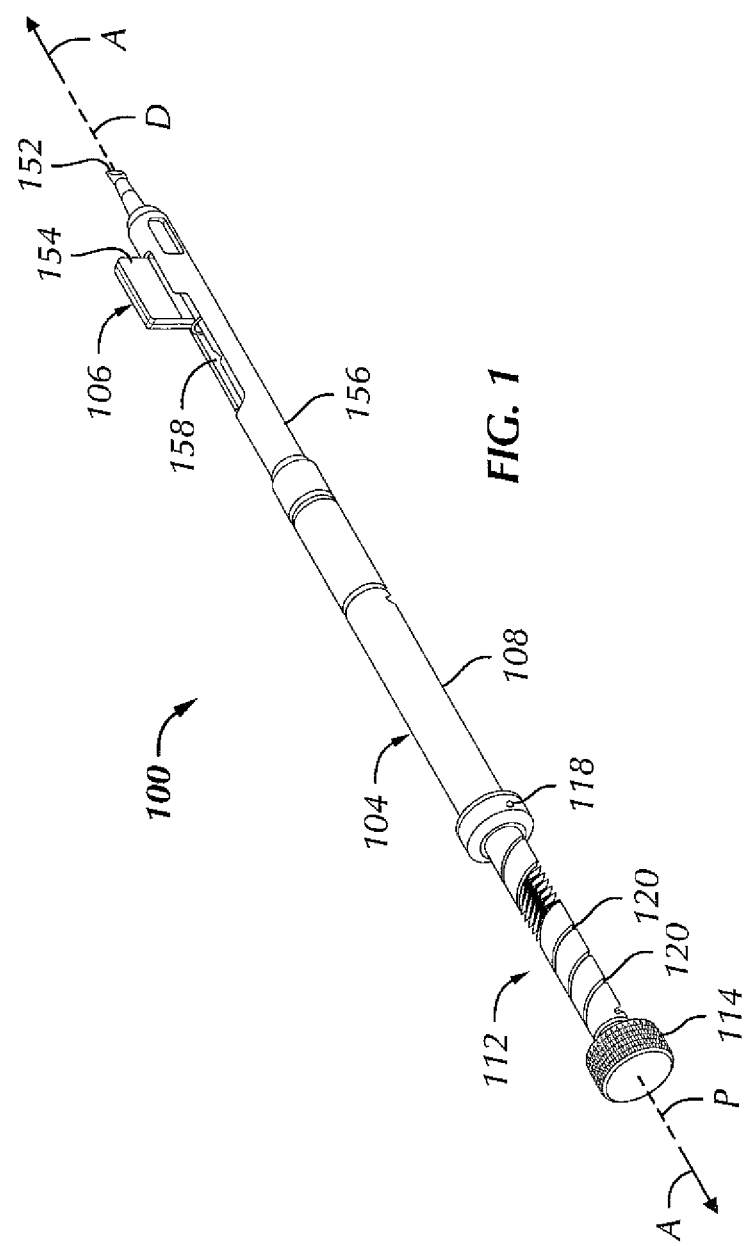
FIG. 1 is a perspective view of an apparatus for inserting an intraocular lens (IOL) into an eye according to a number of embodiments.
Figure 2:
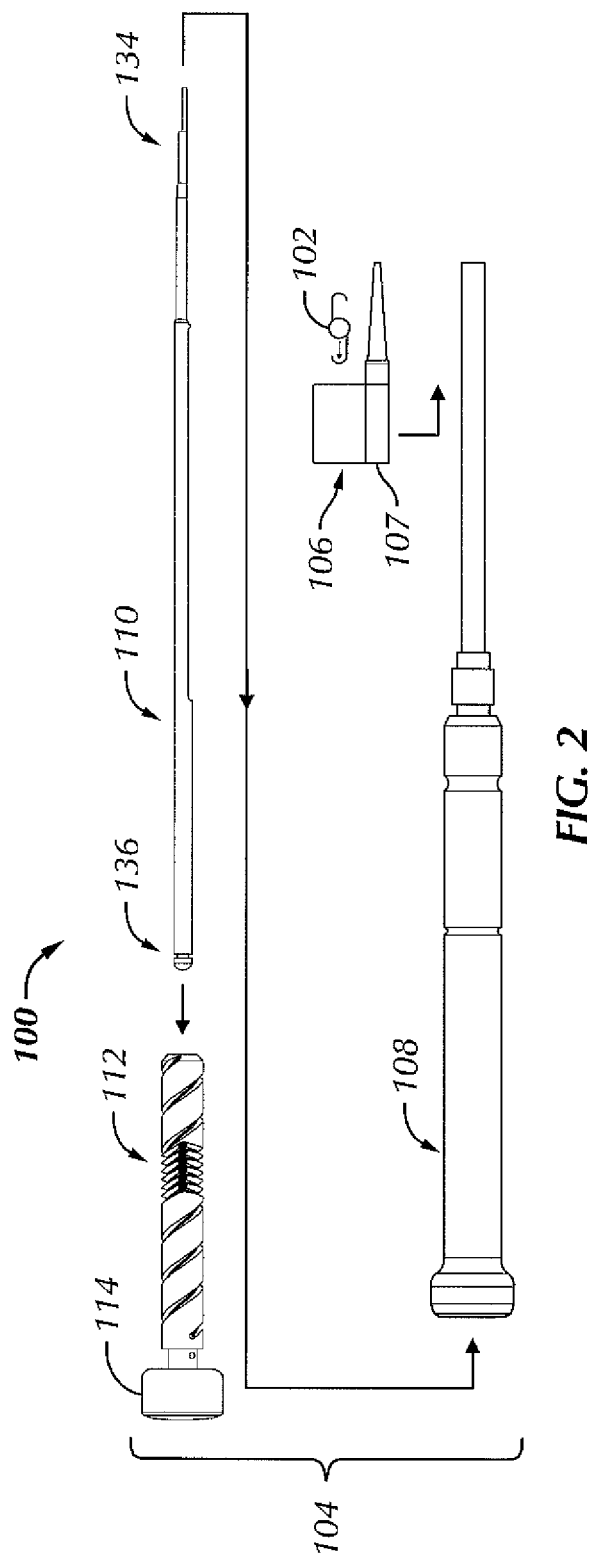
FIG. 2 is an exploded view of the apparatus, particularly illustrating an embodiment in which a drive member is operatively coupled to an injector rod.

Referring to FIGS. 1 and 2, an apparatus 100 for inserting an intraocular lens (IOL) 102 into an eye includes a handpiece 104 and a cartridge 106 containing a load chamber 107 (see also FIG. 15) for receiving the IOL 102. In a number of embodiments, the handpiece 104 may include a body member 108 and an injector rod 110. In other embodiments, the handpiece 104 may additionally include a drive mechanism 112 which, in turn, may include a drive member 114 that is operatively coupled to the injector rod 110.

Figure 3:
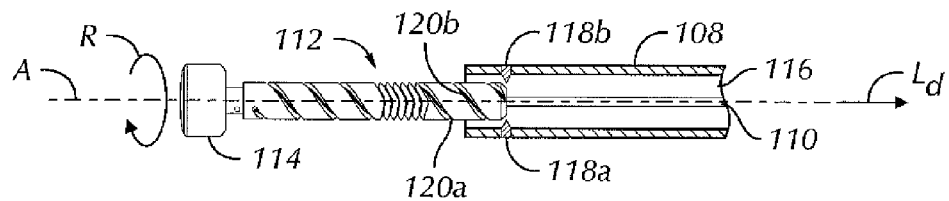
FIG. 3 is a fragmentary cross-sectional view of a drive member, a body member, and an injector rod, particularly illustrating of an initial step of a drive mechanism moving an injector rod longitudinally under a rotational force.

With additional reference to FIG. 3, the body member 108 may include a longitudinal through channel 116. In addition, the drive mechanism 112 may include one or more bosses 118 disposed on the body member 108 and projecting into the channel 116, and a corresponding number of annular races 120 disposed on the drive mechanism 112. In the embodiment illustrated in the figures, the drive mechanism 112 includes a pair of bosses 118a and 118b and a pair of races 120a and 120b. In embodiments in which the drive mechanism 112 and the injector rod 110 are unitary, the annular race 120 may be described as being disposed on the injector rod 110 itself.

For the purposes of this description, the word boss is used to describe any type of structure that is configured to slidingly engage with a race, a thread, a groove, a channel, or similar structure. In addition, the word race is used to describe any type of continuous channel-, thread-, or groove-like structure without breaks or abrupt changes in form. Although the drive mechanism 112 may include a plurality of bosses and races, the drive mechanism 112 may include only a single boss and/or race. The various embodiments are often described herein in the singular for ease of language. Further, as shown in FIG. 1, the apparatus 100 may be described as having a longitudinal axis A with a distal direction D and a proximal direction P.

Figure 4A:
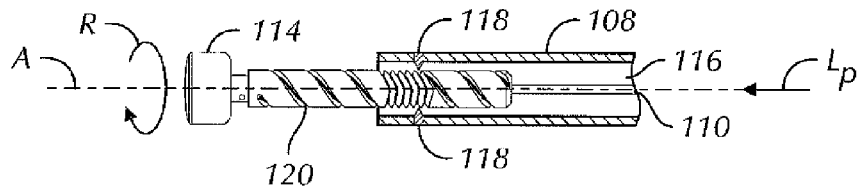
Figure 5B:
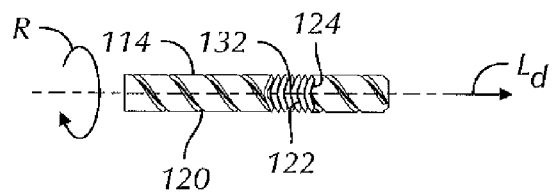
FIGS. 5A and 5B illustrate steps subsequent to that shown in FIGS. 4A and 4B.
Figure 5A:
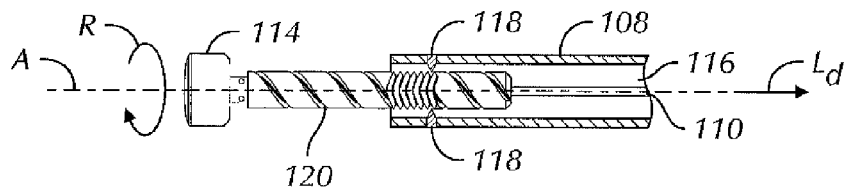

As shown in FIG. 3, the races 120 are configured to engage with the bosses 118, respectively, when the injector rod 110 is at least partially received in the channel 116. With additional reference to FIG. 4A, in a number of embodiments, the race or races 120 are configured so that when the drive member 114 is rotated in a single direction about a longitudinal axis A, as indicated by arrow R, the injector rod 110 moves longitudinally in a first direction as indicated by arrow $L_d$ in FIG. 3 and moves longitudinally in a second direction as indicated by arrow $L_p$ in FIG. 4A that is opposite to the first direction $L_d$. The race or races 120 may also be configured so that with continued rotation in the single direction R, the injector rod 110 moves longitudinally in the first direction again as indicated by arrow $L_d$ as shown in FIG. 5A.

Figure 6:
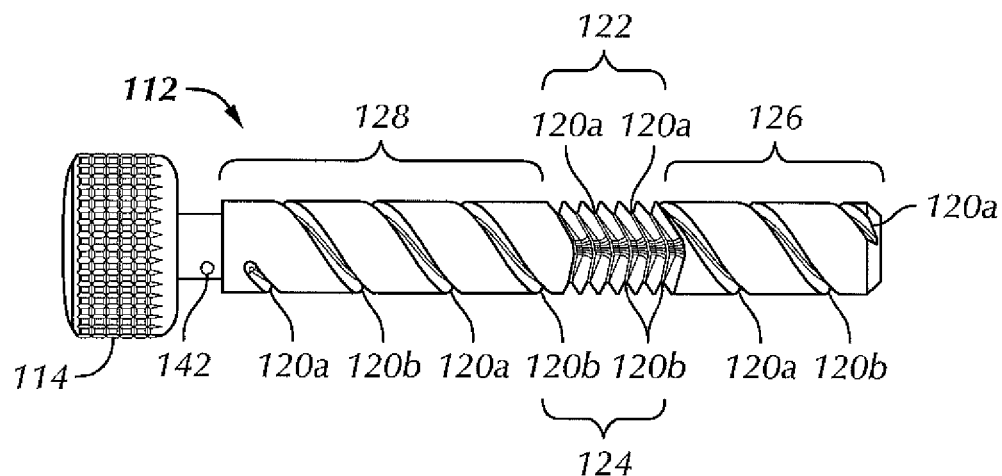
FIG. 6 illustrates a drive member according to a number of embodiments.

More specifically and with reference to FIG. 6, in some of the embodiments, each of the races 120 may include a plurality of distal sections 122 in which the race 120 moves the drive mechanism 112 in the distal direction when the drive member 114 is rotated in a single direction (e.g., as indicated by arrow R in FIGS. 3-5), and a plurality of proximal sections 124 in which the race 120 moves the drive mechanism 112 in the proximal direction when the drive member 114 is rotated in the same single direction (e.g., as indicated by arrow R in FIGS. 3-5). Approximately one half of the distal and proximal sections 122 and 124 in a typical embodiment are illustrated in FIG. 6, with approximately an equal number of distal and proximal sections 122 and 124 being disposed on the other side of the drive mechanism 112 not shown in FIG. 6.

In other embodiments, each of the races 120 may also include an initial section 126 and a final section 128 in each of which the race 120 moves the drive mechanism 112 in the proximal direction when the drive member 114 is rotated in the same single direction (e.g., as indicated by arrow R in FIGS. 3-5). As shown in the embodiment of FIG. 6, the pitch of the race 120 in the distal and proximal sections 122 and 124 may be greater than the pitch of the race 120 in the initial and final sections 126 and 128. Alternatively, the pitch of the race 120 in the distal and proximal sections 122 and 124 may be less than or equal to the pitch of the race 120 in the initial and final sections 126 and 128.

In a number of embodiments, the distal and proximal sections 122 and 124 may successively alternate at predetermined or discrete increments about the drive mechanism 112, for example, approximately 90-degree increments about the drive mechanism 112. In such embodiments, the slope of the distal sections 122 may be greater than the slope of the proximal sections 124 (as illustrated in FIG. 6). In other embodiments, the predetermined or discrete increments about the drive mechanism 112 may be different for the distal and proximal sections 122 and 124. For example, the distal sections 122 may comprise 120-degree increments, while the proximal sections 124 may comprise 60-degree increments. In such embodiments, the slope of the distal sections 122 and the proximal sections 124 may be configured to be approximately equal. Those skilled in the art will appreciate other configurations of the distal and proximal sections 122 and 124 not specifically shown but that cause the injector rod to move distally and proximally as described above. For instance, in order to vary the pattern of longitudinal motion of the drive mechanism 112 as the drive member 114 is turned, the predetermined increments about the drive mechanism 112 may vary over one or more revolutions around the race 120 as compared to the predetermined increments over the remaining revolutions around the race 120. For example, over the first three revolutions around the race 120, the predetermined increment for the distal and proximal sections 122 and 124 may each be 90 degrees, while over the remaining revolutions around the race 120, the predetermined increment for the distal and proximal sections 122 and 124 may each be 120 degrees and 60 degrees, respectively. Additionally, in contrast to FIG. 6, the angle, relative to the longitudinal axis A, of one or more of the individual race portions within the distal and/or proximal sections 122 and 124 may differ from remaining race portions within the distal and proximal sections 122 and 124.

For the purposes of this description the word discrete refers to a magnitude or a distance that is fixed, predetermined, or indexed but that is not determined, set, or varied by user intervention, judgment, or "feel" during a surgical procedure Those skilled in the art will appreciate that a discrete distance thus described may vary slightly due to manufacturing tolerances.

Figure 4B:
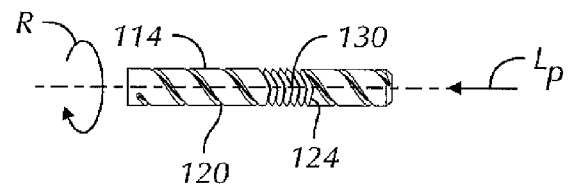
FIGS. 4A and 4B illustrate steps subsequent to that shown in FIG. 3.
Figure 7:
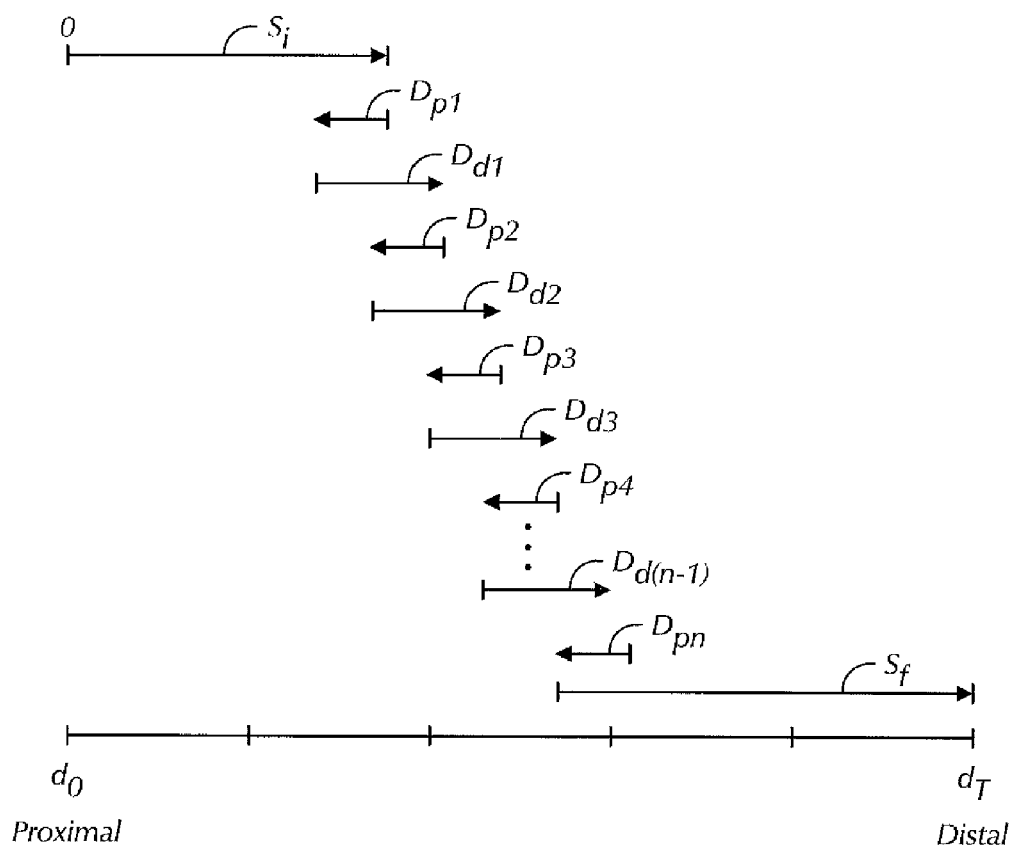
FIG. 7 graphically illustrates discrete distal and proximal increments of longitudinal movement of an injector rod caused by a some of the embodiments of a drive mechanism.

Accordingly, with additional reference to FIG. 7, when the race 120 is engaged with the boss 118 and a rotational force is applied about the axis A such that the drive member 114 and mechanism 112 are rotated in a single rotational direction R (for example, clockwise when viewed from proximal side P, as shown in FIG. 3), the injector rod 110 moves distally an initial predetermined discrete increment $S_i$. When the boss 118 moves relatively within the race 120 beyond a first one of a plurality proximal inflection points 130 as shown in FIG. 4B and moves into a first one of the proximal sections 124, the injector rod 110 moves proximally a first predetermined proximal increment $D_{p1}$. With continued rotation in direction R, when the boss 118 moves relatively within the race 120 beyond a first one of a plurality of distal inflection points 132 as shown in FIG. 5B, and moves into a subsequent first one of the distal sections 122, the injector rod 110 moves distally a first predetermined distal increment $D_{d1}$.

For purposes of this description, the term proximal inflection point 130 is used to describe a point in the race 120 at which the injector rod 110 changes from distal movement to proximal movement with continued rotation of the drive member 114, and the term distal inflection point 132 is used to describe a point in the race 120 at which the injector rod 110 changes from proximal movement to distal movement with continued rotation of the drive member 114.

The back-and-forth or oscillating movement of the injector rod 110 continues with continued rotation of the drive member 114 in the single rotational direction R through successive distal and proximal sections 122 and 124 of the race 120, thereby resulting in successively alternated predetermined discrete or indexed distal and proximal increments $D_{d2}$, $D_{p2}$, $D_{d3}$, $D_{p3}$, $D_{d4}$, ... $D_{d(n-1)}$, and $D_{pn}$, with n being the number of proximal sections 124 in the plurality of proximal sections 124. Continued rotation of the drive member 114 in the rotational direction R may then result in a final predetermined discrete increment $S_f$ through the final section 128 of the race 120.

As shown in FIG. 7, in a number of embodiments, the race 120 may be configured so that the discrete proximal increments $D_p$ are larger than the discrete distal increments $D_d$. For example, the race 120 may be configured so that the distal increments $D_d$ are approximately twice as large as the proximal increments $D_p$. Accordingly, this oscillating incremental longitudinal movement in the distal direction may be described as a two-steps-forward, one-step-backward-type of movement. Alternatively, the distal increments $D_d$ may be greater than or less than twice as large as the proximal increments $D_p$. For instance, the distal increments $D_d$ may be between 2 and 5 times as large as the proximal increments $D_p$, or even larger. In certain embodiments, there may be a limit as to how close in magnitude the proximal increments $D_p$ may be to the distal increments $D_d$, for instance to prevent the races 120 from crossing one another. In yet other embodiments, distal increments $D_d$, the proximal increments $D_p$, or both the distal and proximal increments $D_d$, $D_p$, may varying in size along the drive mechanism 112. For example, the proximal increments $D_{p1}$ and $D_{p2}$ may be one half as large as the distal increment $D_{d1}$, while the proximal increments $D_{p3}$ through $D_{pn}$ may be one quarter as large as the distal increment $D_{d1}$.

The race 120 may be configured so that the injector rod 110 moves from an initial distance $d_0$ to a total distance $d_T$ in the distal direction under a continuous rotational force R in a single direction. From the position $d_T$, rotation of the drive member 114 in an opposite rotational direction (e.g., counter-clockwise) will reverse the movement in the proximal direction. This movement of the injector rod 110 in relation to an IOL is described in more detail below.

Preferably, the distal and proximal sections 122 and 124 of the race 120 are disposed along one portion of the drive member 114, as illustrated in FIG. 6, providing a single portion along the race 120 wherein the injection rod moves in the reciprocating or oscillatory motion illustrated in FIG. 7 by the successive distal and proximal increments $D_d$, $D_p$. Alternatively, portions of the distal and proximal sections 122 and 124 may disposed at different locations along the drive member 114 so as to provide a reciprocating or oscillatory motion at various locations along the race 120. For example, a first set of distal and proximal sections 122 and 124 spanning one or more revolutions of the race 120 may disposed along a first portion of the race 120, while a second set of distal and proximal sections 122 and 124 spanning one or more revolutions of the race 120 may disposed along a second portion of the race 120. In such embodiments, a third portion of the race 120 may be disposed between the first and second portions of the race 120 such that the third portion has a pitch that is similar to that of the race 120 over the initial section 126 and/or a final section 128. Alternatively, the third portion of the race 120 may a different pitch or configuration. For instance, the third portion of the race 120 may be configured to run parallel to the longitudinal axis A.

In certain ophthalmic applications, the distal increments $D_d$ and the proximal increments $D_p$ are preferably less than about 0.5 inches, more preferably less than about 0.25 inches, and even more preferably less than about 0.1 inches to about 0.05 inches. In other embodiments at least one of distal increments $D_d$ and the proximal increments $D_p$ are greater than about 0.5 inches. In one particularly useful embodiment, the distal increments $D_d$ are approximately 0.10 inches and the proximal increments $D_p$ are approximately 0.05 inches. In other applications, outside of ophthalmic applications, the distal increments $D_d$ and the proximal increments $D_p$ may be within these ranges or outside these ranges, depending upon the magnitude of reciprocating motion that is desired for a particular application. For example, the drive mechanism may be part of a MEMS or nanotechnology device, in which case the distal increments $D_d$ and the proximal increments $D_p$ are preferably within a range more suited to the size of the particular device, for instance in a range of about 1 micron to about 500 microns or in a range of about 1 nanometer to about 1000 nanometers. In other embodiments and/or applications the distal increments $D_d$ and the proximal increments $D_p$ are much larger than those already mentioned, for example in the range of about one-half inch to about 12 inches or in a range of about 1 foot to about 6 feet or more.

Figure 8:
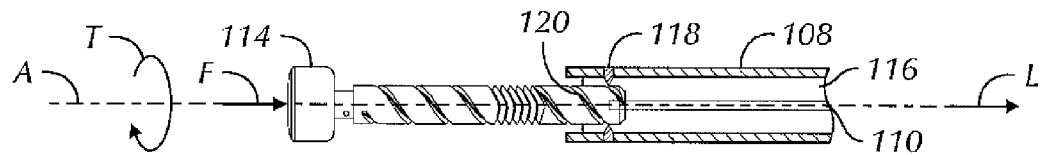
FIG. 8 is a fragmentary cross-section view of a drive member, a body member, and an injector rod, particularly illustrating of an initial step of a drive mechanism moving an injector rod longitudinally under alternating longitudinal and rotational forces.
Figure 9A:
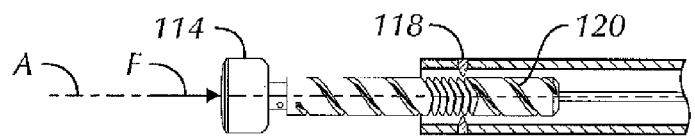
FIGS. 9A and 9B illustrate steps subsequent to that shown in FIG. 8.
Figure 9B:
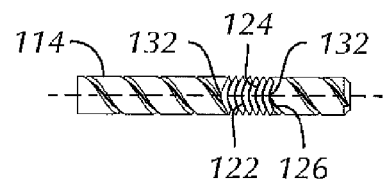

In certain embodiments, the drive mechanism 112 may also move the injector rod 110 longitudinally in the distal and/or proximal directions as the result of an axial force or forces, or under a combination of axial and rotational forces. More specifically, as shown in FIG. 8, the race 120 is engaged with the boss 118, a longitudinal force F may be axially applied to the drive member 114, thereby causing the drive member 114 and mechanism 112 to rotate in a rotational direction T about axis A relative to the body member 108 and causing the injector rod 110 to move in a first direction, i.e., distally, as shown by arrow L. The injector rod 110 moves distally to a first point at which the injector rod 110 is prevented from further rotation and, therefore, further longitudinal movement. This first brake point is the point at which the boss 118 is positioned in the first one of the plurality of distal inflection points 132 defined between the initial section 126 of the race 120 and the first one of the distal sections 124 of the race, can be seen in FIGS. 9A and 9B. At this first one of the distal inflection points 132, and at all subsequent distal inflection points 132, the drive member 114 will not rotate regardless of the magnitude of the longitudinal force F applied. Accordingly, the injector rod 110 is prevented from moving distally.

Figure 10:
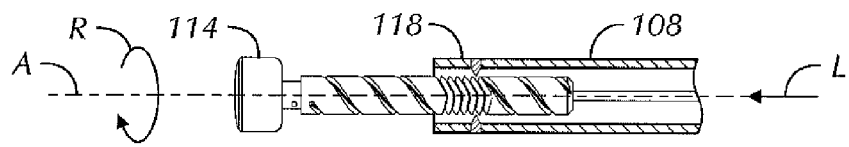
FIG. 10 illustrates a step subsequent to that shown in FIGS. 9A and 9B.
Figure 11B:
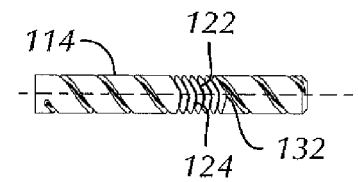
FIGS. 11A and 11B illustrate steps subsequent to that shown in FIG. 10.
Figure 11A:
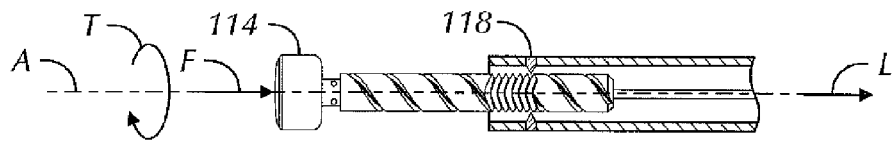

To move the injector rod 110 proximally the first discrete proximal increment $D_{p1}$ as shown in FIG. 7, a rotational force R may be applied as shown in FIG. 10 in the same direction as the rotational direction T, thereby causing the injector rod 110 to move proximally as shown by arrow L. At the subsequent proximal inflection point 130 as can be seen in FIGS. 11A and 11B, the longitudinal force F may once again be applied, thereby causing the drive member 114 to rotate in the same rotational direction T and to move distally the first discrete distal increment $D_{d1}$. By alternating the longitudinal and rotational forces F and R in this manner, the injector rod 110 moves incrementally in the distal direction as shown in FIG. 7.

The longitudinal movement of the injector rod 110 may be a translation or may also be a rotation. More specifically, in embodiments in which the drive mechanism 112 is fixed to or unitary with the injector rod 110, then rotation of the drive member 114 will cause a rotation of the injector rod 110 as well, along with the longitudinal movement thereof. In unitary embodiments in which the drive mechanism 112 may be considered as a proximal portion of the injector rod 110, the injector rod 110 may be described as including the annular race 120, with a rotation of the injector rod 100 causing a longitudinal movement of the injector rod 110.

Figure 12:
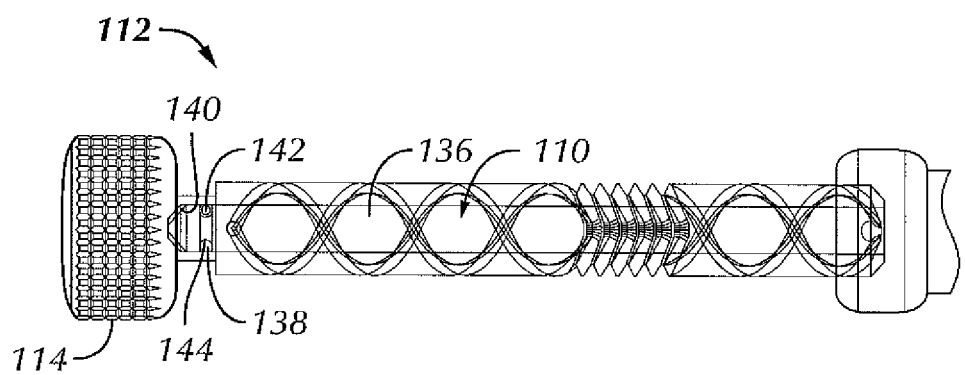
FIG. 12 illustrates a drive member operatively coupled with an injector rod according to a number of embodiments.

In embodiments in which the injector rod 110 is operatively coupled to the drive mechanism 112 in an independently rotating manner, then rotation of the drive member 114 will cause a translation of the injector rod 110 with essentially minimal or no rotation. For example, with reference to FIGS. 2 and 12, the injector rod 110 may include a distal end 134 adapted to contact an IOL 102 and a proximal end 136 for engaging with the drive mechanism 112. The drive mechanism 112 may include a longitudinal channel or recess 138 with a seat 140 adapted to rotatingly receive the proximal end 136 of the injector rod 110. A pin 142 may be provided to retain the injector rod 110 by being received in an annular channel 144 thereof. Accordingly, the injector rod 110 is able to rotate relative to the mechanism 112 and the drive. Other mechanisms or means may alternatively be used to couple the drive mechanism 112 to the injector rod 110 so that the mechanism 112 and the drive member 114 are able to rotate independently of the injector rod 110.

Figure 13:
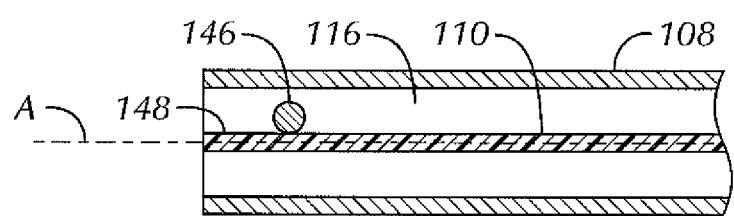
FIG. 13 is a fragmentary cross-sectional view of a body member and an injector rod according to some of the embodiments in which the injector rod translates.
Figure 14:
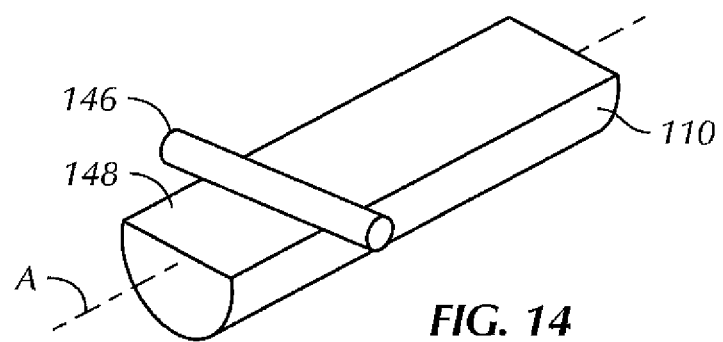
FIG. 14 is a perspective view illustrating the embodiment of FIG. 13.

To prevent at least the distal portion 134 of the injector rod 110 from rotating during longitudinal movement, a retaining structure may be provided. For example, as shown in FIGS. 13 and 14, the body member 108 may include a pin 146 disposed transversely across the channel 116, and the injector rod 110 may include a chamfer 148 along a longitudinal portion thereof for engaging with the pin 146. Accordingly, when the drive member 114 is rotating to incrementally drive the injector rod 110, any rotation of the injector rod 110 is dampened or prevented by the pin 146 and the chamfer 148, thereby resulting in only a translation of the injector rod 110.

For the purposes of this description, translate is used to describe a change in the position of the injector rod 110 in space without substantial rotation. Depending upon the tolerance of a manufactured handpiece 104, there may be an initial slight rotation of a few degrees prior to the chamfer 148 engaging the pin 146 and a slight rotation of a few degrees when the chamfer 148 disengages with the pin 146. In addition, the term oscillate is used to describe a plurality of linear or longitudinal back-and-forth movements of the injector rod 110 in the distal and proximal directions.

Figure 15:
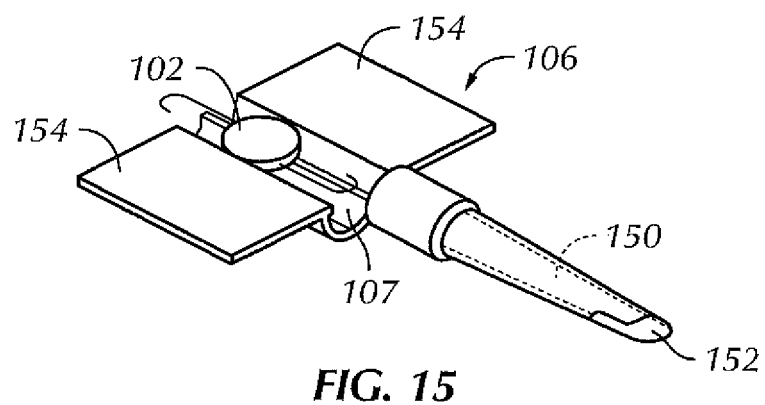
FIG. 15 is a perspective view of a cartridge and an IOL.

Utilization of the apparatus 100 is now described. As shown in FIG. 15, the cartridge 106 may include a hollow passage 150 with an ejection port 152. An IOL 102 may be loaded in the cartridge 106 as known in the art by drawing a pair of tabs 154 together, thereby folding the IOL 102 therein, similar to a hard-shelled taco. The IOL 102 is then passable through the hollow passage 150 and out of the port 152.

Figure 16A:
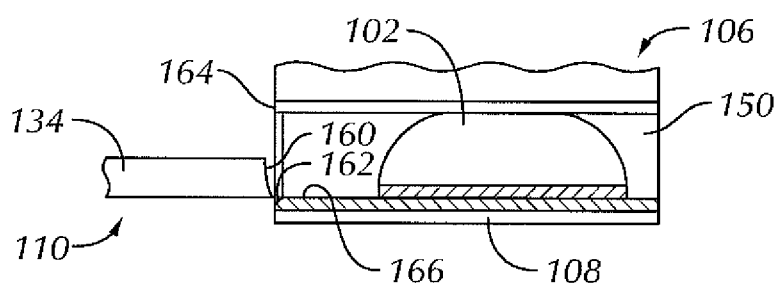
FIGS. 16A and 16B are a partial cross-sectional views illustrating a tip of an injector rod entering a cartridge and contacting an IOL according to some of the embodiments.

When loaded with an IOL 102, the cartridge 106 may be loaded into a distal portion 156 of the body member 108, for example, through a slot 158. The drive mechanism 112 may then be actuated to cause the injector rod 110 to incrementally move in the distal direction. As shown in FIG. 16A, in a number of embodiments, the cartridge 106 may include a chamfered lip 162 on a proximal edge 164 thereof. Accordingly, when a tip 160 of the distal portion 134 of the injector rod 110 reaches the cartridge 106, the tip 160 is urged upwardly by the lip 162, thereby producing an interference fit between the distal portion 134 of the injector rod 110 and a wall 166 of the hollow passage 150 of the cartridge 106. In other words, the resultant downward force of the distal portion 134 biases the tip 160 against the wall 166. In other embodiments, the cartridge 106 may be configured so that the tip 160 is not biased.

In certain embodiments, the IOL 102 is loaded into the cartridge 106 by a practitioner as part of a surgical procedure for delivering the IOL 102 into the eye of a subject. In other embodiments, the cartridge 106 may be preloaded with the IOL 102 prior to shipment to the practitioner. In yet other embodiments, the apparatus 100 may not include a separate cartridge 106 but rather may incorporate the load chamber 107 into the handpiece 104. An example of such an embodiment is provided in U.S. patent application Ser. No. 11/056,501, entitled "Front Loading IOL Insertion Apparatus and Method of Using," the entire disclosure of which is incorporated herein by reference.

Figure 16B:
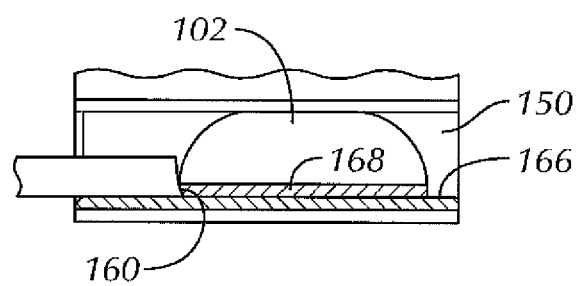

As the drive mechanism 112 is continued to be actuated, the tip 160 of the injector rod 110 contacts an edge 168 of the IOL 102, as shown in FIG. 16B. In a number of embodiments, it may be beneficial for the tip 160 to contact the IOL 102 at the wall 166 because the edge 168 of the IOL tends to locate at that position. When the injector rod 110 moves a distal incremental $D_d$, the IOL 102 is urged distally in the passage 150. However, in contrast with conventional appliances in which the injector rods tended to "ride up" over the edge 168 and, thereby, become engaged with the IOL, the subsequent proximal increment $D_p$ of the injector rod 110 backs the tip 160 away from the IOL 102, minimizing the chance of engaging the IOL. During the proximal increment, the IOL 102 may then at least partially restore any deformation caused by the tip 160 during the previous distal increment under its own resiliency. The longitudinal linear oscillation of the injector rod 110 discretely and incrementally urges the IOL through the passage 150.

In a number of embodiments, the tip 160 of the injector rod 110 may be beveled or, alternatively, configured in a concave manner as shown in FIG. 16B. Accordingly, as the rod 110 moves distally and contacts the IOL 102, the tip 160 is urged outwardly or downwardly against the wall 166.

According to a number of embodiments, to minimize or prevent engagement with a typical acrylic IOL, the drive mechanism 112 may be configured so that the distal increments $D_d$ are approximately 0.10 inch and the proximal increments $D_p$ are approximately 0.05 inch. In other embodiments, the drive mechanism 112 may be configured so that the distal increments $D_d$ are approximately 0.050 inch and the proximal increments $D_p$ are approximately 0.025 inch. Generally speaking, the distal increment $D_d$ may be about twice as large as the proximal increment $D_p$, although other ratios may be alternatively used.

Figure 17:
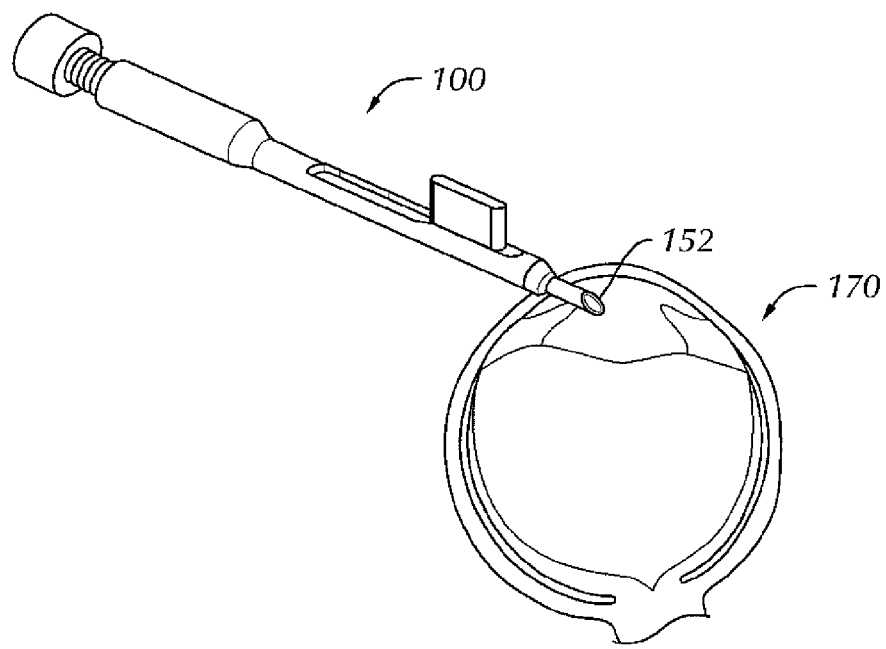
FIG. 17 illustrates an embodiment of an apparatus inserting an IOL into an eye.

The port 152 of the cartridge 106 may be positioned in an eye 170 as shown in FIG. 17 according to known procedures. The continued actuation of the drive mechanism 112 as described above results in the injector rod 110 urging the IOL 102 through the cartridge 106 and toward the eye 170.

Figure 18:
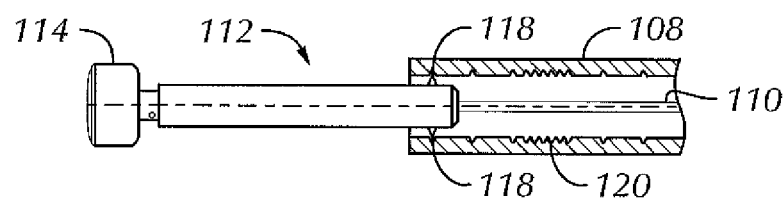
FIG. 18 is a fragmentary cross-section view of a handpiece shown according to alternative embodiments.

Those skilled in the art will understand that the preceding exemplary embodiments of the present invention provide the foundation for numerous alternatives and modifications thereto. For example, as shown in FIG. 18, the drive mechanism 112 may be configured so that the annular race 120 is disposed on an inner wall of the body member 108 of the handpiece 104, with the boss 118 being disposed on the drive mechanism 112.

In other embodiments, the drive mechanism 112 may include an electro-mechanical drive means such as a motor to actuate the drive member 114. In other embodiments, a control circuit may monitor, for example, torque so that the proximal increment is triggered when torque reaches a threshold.

Figure 19:
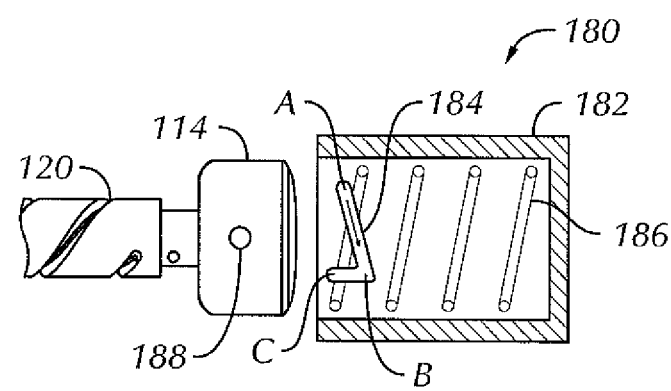
FIG. 19 is a fragmentary cross-sectional view of a torque release mechanism for a handpiece.

Alternatively, a mechanical device 180 for actuating in response to torque may be provided as shown in FIG. 19. The device 180 may include a cap-like housing 182 with a slot 184 and a compression spring 186. A boss 188 may be disposed on the drive member 114 so that when the housing 182 is received over a proximal end of the drive member 114, the boss 188 is received in the slot 184 at position A. In operation, when the housing 182 is rotated, any increase in torque on the drive member 114 will cause the boss 188 to slide in the slot 184 as indicated by the arrow, thereby compressing the spring 186. When the torque reaches a predetermined level as determined by the selected spring 186, the boss 188 will be located at position B, and will then be forced to position C by the force of the spring 186, thereby causing the drive member 114 to snap or move proximally the distance between positions B and C. The slot 184 may be repeated annularly in the housing 182 so that this process may repeat.

These and other modifications are also within the scope of the present invention. Accordingly, the present invention is not limited to that precisely as shown and described above but by the scope of the appended claims.

What is claimed is:

1. A method for inserting an intraocular lens (IOL) into an eye utilizing an apparatus comprising: a load chamber for receiving an IOL and including a hollow passage with an ejection port through which the IOL is passable; and a handpiece including: a body member disposed about a longitudinal axis; an injector rod that is receivable by the body member and that is longitudinally movable within the hollow passage, the injector rod having a distal end adapted to contact the IOL when positioned within body member; and a drive mechanism disposed about a longitudinal axis coupled to the injector rod comprising: a drive member; a guide; and a follower coupled to the guide, the method comprising:

causing the injector rod to move back and forth discretely a plurality of times in distal increments and proximal increments, wherein the injector rod advances toward an ejection port along a path that longitudinally moves the injector rod back and forth in the body member a plurality of times when a rotational force is applied about the longitudinal axis in a single direction, and wherein the drive mechanism oscillates the injector rod longitudinally in increments that are greater in the distal direction than in the proximal direction.

2. The method of claim 1 wherein the distal increments are approximately equal in magnitude and the proximal increments are approximately equal in magnitude.

3. The method of claim 1 further comprising causing the injector rod to move distally a final discrete predetermined increment after a last one of the distal increments.

4. The method of claim 1 wherein the distal increments are approximately twice as large as the proximal increments.

5. The method of claim 1, wherein the distal increments are successively alternated with the proximal increments; and each of the distal increments is greater than each of the proximal increments.

6. The method of claim 1, wherein the injector rod advances distally a first predetermined increment; then the injector rod advances proximally a second predetermined increment that is less than the first predetermined increment; and then the injector rod advances distally a third predetermined increment.

7. The method of claim 1, wherein the proximal increments and distal increments are predetermined.

* * * * *